(12) United States Patent
Ford et al.

(10) Patent No.: US 9,334,292 B2
(45) Date of Patent: May 10, 2016

(54) ALKALINE EARTH METAL-COMPLEXED METAL BISAMIDES

(71) Applicants: BAYER INTELLECTUAL PROPERTY GMBH, Monheim (DE); BAYER CROPSCIENCE AG, Monheim (DE)

(72) Inventors: Mark James Ford, Schmitten (DE); Marc Mosrin, Frankfurt (DE)

(73) Assignees: Bayer Cropscience AG, Monheim am Rhein (DE); Bayer Intellectual Property GmbH, Monheim am Rhein (DE)

( * ) Notice: Subject to any disclaimer, the term of this patent is extended or adjusted under 35 U.S.C. 154(b) by 81 days.

(21) Appl. No.: 14/378,998

(22) PCT Filed: Feb. 13, 2013

(86) PCT No.: PCT/EP2013/052902
§ 371 (c)(1),
(2) Date: Aug. 15, 2014

(87) PCT Pub. No.: WO2013/120911
PCT Pub. Date: Aug. 22, 2013

(65) Prior Publication Data
US 2016/0016977 A1 Jan. 21, 2016

(30) Foreign Application Priority Data

Feb. 17, 2012 (EP) .................................... 12155977
Jun. 13, 2012 (EP) .................................... 12171862

(51) Int. Cl.
*C07F 3/06* (2006.01)
*C07F 3/02* (2006.01)

(52) U.S. Cl.
CPC .......................................... *C07F 3/06* (2013.01)

(58) Field of Classification Search
USPC ................................................. 546/11; 556/28
See application file for complete search history.

(56) References Cited

FOREIGN PATENT DOCUMENTS

| WO | 2008138946 A1 | 11/2008 |
|----|---------------|---------|
| WO | 2010092096 A1 | 2/2010 |

OTHER PUBLICATIONS

International Search Report from corresponding PCT/EP2013/052902, mailed Apr. 22, 2013.
Wunderlich, et al., "(tmp)2Zn-2MgCl2-2 LiCl: A Chemoselective Base for the Directed Zincation of Sensitive Arenes and Heteroarenes", Angew. Chem. Int. Ed. 2007, 46, 7685-7688.

*Primary Examiner* — Charanjit Aulakh
(74) *Attorney, Agent, or Firm* — McBee Moore Woodward Vanik IP PLLC

(57) ABSTRACT

The present invention relates to alkaline earth metal-complexed metal bisamides of the formula (I), to a process for preparation thereof and to the use thereof for metallation of aromatics, heteroaromatics, alkenes, alkynes and other organic compounds having activated C—H bonds.

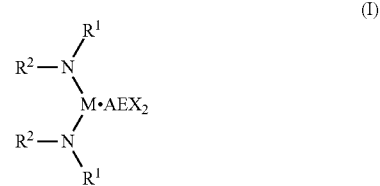

14 Claims, No Drawings

ALKALINE EARTH METAL-COMPLEXED METAL BISAMIDES

CROSS REFERENCE TO RELATED APPLICATIONS

This application is a §371 National Stage Application of PCT/EP2013/052902, filed Feb. 13, 2013, which claims priority to EP 12155977.7, filed Feb. 17, 2012 and EP 12171862.1, filed Jun. 13, 2012.

BACKGROUND

1. Field of the Invention

The present invention relates to alkaline earth metal-complexed metal bisamides of the formula (I), to a process for preparation thereof and to the use thereof for metallation of aromatics, heteroaromatics, alkenes, alkynes and other organic compounds having activated C—H bonds.

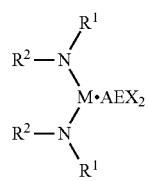
(I)

2. Description of Related Art

The preparation of aromatic and heteroaromatic molecules is of great significance because of the high biological potency thereof. Consequently, these structural elements are constituents of many active pharmaceutical and agrochemical ingredients. Direct metallation has become established as an excellent tool for functionalization of aromatics, heteroaromatics and other organic compounds having activated C—H bonds.

For this purpose, predominantly lithium alkyls or lithium amides have been used to date as bases.

As an alternative, efficient bases have been developed for magnesiation and zincation of aromatics and heteroaromatics. Zinc amide or magnesium amide bases, for example Mg-TMP and Zn-TMP (TMP=2,2,6,6-tetramethylpiperidyl), complexed with lithium chloride, for example TMPMgCl.LiCl, TMPZnCl.LiCl, $TMP_2Zn.2MgCl_2.2LiCl$, are described in WO 2010/092096 and WO 2008/138946 as versatile metallating reagents. They have high kinetic basicity coupled with very good chemo- and regioselectivities. In addition, the zinc amide bases can be stored under protective gas as solutions in THF for weeks, without losing activity.

For synthesis of the bases, typically amines, for example TMP, are lithiated with equimolar amounts of butyllithium. Owing to the high cost of butyllithium, the bases are too expensive for a multitude of industrial syntheses. There is therefore an urgent need for a favourable route to these bases, dispensing with the use of expensive butyllithium.

SUMMARY

The object was achieved in accordance with the invention by a process for preparing alkaline earth metal-complexed metal bisamides of the formula (I) or tautomers thereof

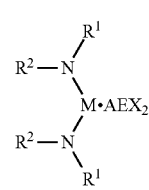
(I)

where
AE is an alkaline earth metal selected from calcium and magnesium;
M is a metal selected from metals from groups 3, 4, 7, 8, 9, 10, 11, 12, 13 of the Periodic Table of the Elements (PTE) and the group of the lanthanoids;
X is a halogen atom selected from the group consisting of fluorine, chlorine, bromine and iodine;
$R^1$ and $R^2$ are each independently selected from the group consisting of $(C_1-C_8)$alkyl optionally substituted by 1-2 $R^3$ radicals;
or
$R^1$ and $R^2$ together form a —$(CH_2)_4$—, —$(CH_2)_5$— or —$(CH_2)_2O(CH_2)_2$— group, where each of these groups may optionally be substituted by 1-4 $R^4$ radicals;
$R^3$ is independently selected from halogen, $(C_1-C_3)$alkoxy, $(C_1-C_3)$haloalkoxy;
$R^4$ is independently selected from halogen, $(C_1-C_3)$alkyl, $(C_1-C_3)$alkoxy, $(C_1-C_3)$haloalkoxy and $(C_2-C_4)$dialkylamino,
by reaction of chloroamines of the formula (II)

$$R^2 \underset{}{\overset{R^1}{\underset{|}{N}}} Cl \qquad (II)$$

in which the $R^1$ and $R^2$ radicals are each as defined above with
(i) metallic magnesium and/or calcium and/or
(ii) a magnesium and/or calcium halide and
(iii) an amount—optionally a substoichiometric amount based on the chloroamine of the formula (II)—of a metal (M) (i.e. in elemental form) and/or
(iv) an amount—optionally a substoichiometric amount—of a metal halide $(M^{n+}X^-_n)$
where M and X are each as defined above.

DETAILED DESCRIPTION OF A PREFERRED EMBODIMENT

The oxidative insertion of the alkaline earth metal (AE), preferably magnesium or calcium, and/or of the metal (M), e.g. zinc or manganese, allows the process according to the invention to dispense with the use of costly butyllithium.

It will be appreciated here that the index n in any metal halide $(M^{n+}X^-_n)$ used in the process according to the invention is an integer corresponding to the valency of the metal ion of the metal (M). Preferably, n=2, 3 or 4, particularly preferably n=2.

Moreover, the magnesium- and calcium-complexed metal bisamides obtainable by the process according to the invention are especially suitable for metallation under mild conditions. They are therefore particularly suitable for conversion of sensitive (hetero)aromatics and are tolerated by sensitive functional groups, for example nitro, aldehyde or F, which is often not the case for the corresponding lithium or magnesium bases.

The reaction of 2-chloro-3-nitropyridine with $(TMP)_2Zn \cdot 2MgCl_2Cl_2 \cdot 2LiCl$ is described in the literature (see Angew. Chem. Int. Ed. 2007, 46, 7685-7688). The metallation was performed therein at −40° C. for 1.5 h, followed by reaction with an electrophile. However, in-house studies have shown that the metallation of 2-chloro-3-nitropyridine using $(TMP)_2Zn \cdot 2MgCl_2 \cdot 2LiCl$ at higher temperatures, especially at temperatures above 10° C., for example at 25° C., leads to the destruction of the 2-chloro-3-nitropyridine. If the reaction of the 2-chloro-3-nitropyridine, in contrast, is performed under the same conditions with an inventive alkaline earth metal-complexed metal bisamide of the formula (I), the desired metallation proceeds at temperatures above 10° C. within a very short time (in the specific example: 1 minute at 25° C.), and likewise the subsequent reaction with an electrophile "E". Such a reaction is shown below, using the example of the inventive $(TMP)_2Zn \cdot MgCl_2$.

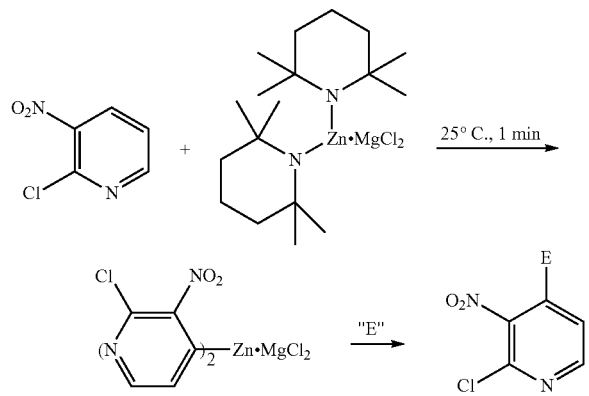

The corresponding metallation and subsequent Negishi coupling with ethyl 4-iodobenzoate (as electrophile "E") gave the desired compound in 58% yield (see example below).

The term "halogen" or "halogen atom" means, for example, fluorine, chlorine, bromine or iodine. When the term is used for a radical, "halogen" or "halogen atom" means, for example, a fluorine, chlorine, bromine or iodine atom.

Alkyl means a straight-chain, branched or cyclic hydrocarbyl radical. The expression "$(C_1-C_4)$alkyl", for example, is a brief notation for alkyl having one to 4 carbon atoms according to the range stated for carbon atoms and encompasses, for example, the methyl, ethyl, 1-propyl, 2-propyl, 1-butyl, 2-butyl, 2-methylpropyl, tert-butyl, cyclopropyl and cyclobutyl radicals. General alkyl radicals with a larger specified range of carbon atoms,
e.g. "$(C_1-C_6)$alkyl", correspondingly also encompass straight-chain, branched or cyclic alkyl radicals with a greater number of carbon atoms, i.e. according to the example also the alkyl radicals having 5 and 6 carbon atoms.

Unless stated specifically, for the hydrocarbyl radicals such as alkyl radicals, including in composite radicals, preference is given to the lower carbon skeletons, for example having 1 to 6 carbon atoms, or having 2 to 6 carbon atoms in the case of unsaturated groups. Alkyl radicals, including in the composite radicals such as alkoxy, haloalkyl etc., mean, for example, methyl, ethyl, cyclo-, n- or i-propyl, cyclo-, n-, i-, t- or 2-butyl, pentyls, hexyls such as cyclohexyl, n-hexyl, i-hexyl and 1,3-dimethylbutyl, heptyls such as cycloheptyl, n-heptyl, 1-methylhexyl and 1,4-dimethylpentyl.

Preferred cyclic alkyl radicals preferably have 3-8 ring carbon atoms, for example cyclopropyl, cyclobutyl, cyclopentyl or cyclohexyl. In the case of optionally substituted cyclic alkyl radicals, cyclic systems with substituents are included, also including substituents with a double bond on the cyclic alkyl radical, for example an alkylidene group such as methylidene.

In the case of optionally substituted cyclic alkyl radicals, polycyclic aliphatic systems are also included, such as bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl. In the case of optionally substituted cyclic alkyl radicals, spirocyclic aliphatic systems are also included, for example spiro[2.2]pent-1-yl, spiro[2.3]hex-1-yl, spiro[2.3]hex-4-yl, 3-spiro[2.3]hex-5-yl.

Aryl is a mono-, bi- or polycyclic aromatic system having preferably 6 to 14, especially 6 to 10, ring carbon atoms, for example phenyl, indanyl, naphthyl, anthryl, phenanthrenyl and the like, preferably phenyl. When two or more radicals form one or more rings, these may be carbocyclic, heterocyclic, saturated, partly saturated, unsaturated, for example also aromatic and optionally further substituted. The fused rings are preferably 5- or 6-membered rings, particular preference being given to benzofused cycles.

The substituents mentioned by way of example ("first substituent level") may, if they contain hydrocarbonaceous moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example, halogen, nitro, cyanoalkyl, dialkylamino, alkoxy, aryl, aryloxy, benzyl, benzyloxy, heterocyclyl and trialkylsilyl.

Substituents composed of more than one substituent level are preferably, for example, alkoxyalkyl such as monoalkoxyalkyl or dialkoxyalkyl, alkoxyalkoxy such as monoalkoxyalkoxy or dialkoxyalkoxy, benzyl, phenethyl, benzyloxy, haloalkyl, haloalkoxy, haloalkoxyalkoxy, haloalkoxyalkyl.

In the case of radicals having carbon atoms, preference is given to those having 1 to 6 carbon atoms, preferably 1 to 4 carbon atoms, especially 1 or 2 carbon atoms. Preference is generally given to substituents from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino such as mono- or disubstituted amino is a radical from the group of the substituted amino radicals which are N-substituted, for example, by one or two identical or different radicals from the group of alkyl, alkoxy and aryl; preferably dialkylamino and diarylamino, such as optionally substituted N-alkyl-N-arylamino, and saturated N-heterocycles; preference is given to alkyl radicals having 1 to 4 carbon atoms; aryl is preferably phenyl or substituted phenyl.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$alkoxy- ($C_1$-$C_4$)alkoxy, ($C_1$-$C_4$)alkoxy-($C_1$-$C_4$)alkyl, ($C_1$-$C_4$)haloalkyl, ($C_1$-$C_4$)haloalkoxy, cyano and nitro, e.g. o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted heterocyclyl is preferably heterocyclyl which is unsubstituted or mono- or polysubstituted, preferably up to trisubstituted, by identical or different radicals from the group of halogen, cyano, ($C_1$-$C_4$)alkyl, ($C_1$-$C_4$)alkoxy, ($C_1$-$C_4$)alkoxy-($C_1$-$C_4$)alkoxy, ($C_1$-$C_4$)alkoxy-($C_1$-$C_4$)alkyl, ($C_1$-$C_4$)haloalkyl, ($C_1$-$C_4$)haloalkoxy, nitro and oxo, and is especially mono- or polysubstituted by radicals from the group of halogen, ($C_1$-$C_4$)alkyl, ($C_1$-$C_4$)alkoxy, ($C_1$-$C_4$)haloalkyl and oxo, very particularly by one or two ($C_1$-$C_4$)alkyl radicals.

Haloalkyl is alkyl partly or fully substituted by identical or different halogen atoms, for example monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2CHFCl$, $CHCl_2$, $CF_2CF_2H$, $CH_2CF_3$; haloalkoxy is, for example, $OCF_3$, $OCHF_2$, $OCH_2F$, $OCF_2CF_3$, $OCH_2CF_3$ and $OCH_2CH_2Cl$.

Tautomers of the alkaline earth metal-complexed metal bisamides of the formula (I) are isomers which are interconverted rapidly by the migration of individual atoms or atom groups, meaning that several isomers are in a rapid chemical equilibrium with one another. Owing to the rapid equilibrium, the individual tautomers often cannot be isolated; the ratio of the tautomers relative to one another is typically constant.

Organic compounds having activated C—H bonds are molecules having an increased tendency to release a hydrogen atom bonded to a carbon atom as protons, and hence, in a formal sense, to act as an acid. This is the case, for example, when the carbon atom is bonded to strongly electron-withdrawing groups such as carbonyls (in an ester, ketone or aldehyde), sulphones, nitriles, trifluoromethyl groups or nitro groups. For example, derivatives of malonic acid (pKa≈13) or acetylacetone (pKa≈9) have activated C—H bonds. C—C multiple bonds, as a result of the proximity of the carbon atoms, likewise ensure stronger polarization, such that α-alkenyl and -alkynyl groups, as, for example, in vinyl and propargyl groups, lead to CH activation. In addition, the formation of aromatic systems can also enhance CH acidity.

For the metal bisamides of the formula (I), for example, the tautomer equilibrium shown in Scheme 1 below can be postulated:

Scheme 1:

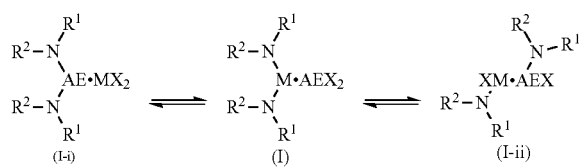

(I-i)    (I)    (I-ii)

The formula (I) therefore also encompasses all tautomers (I-i, I and I-ii) and/or their oligomeric or polymeric complexes present in equilibrium, in which coordinating solvents may optionally also be involved in the structures formed. The bond may be formed either via the halides X or via the nitrogen atoms.

The process according to the invention is to be described in detail by the example, shown in Scheme 2 below, of the preparation of $(TMP)_2Zn\cdot MgCl_2$.

Scheme 2:

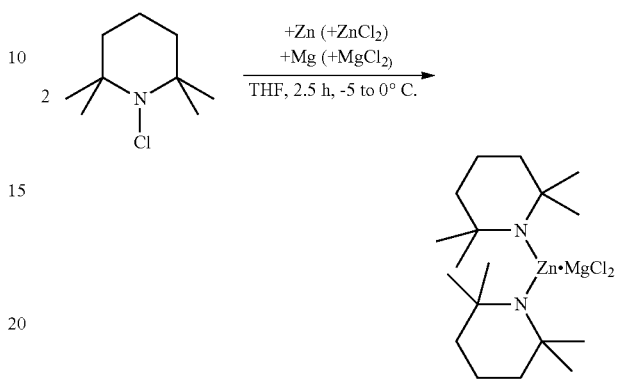

The chloroamines of the formula (II) can be obtained by the methods described in the prior art, for example in Bodor et al. Jour. Pharm. Sci. 1974, 63, 1387; Kovacic et al., Chemical Reviews 1970, 70, 6, 639; Zakrzewski et al, Synthetic Communications 1988, 18(16&17), 2135; J. Org. Chem. 1997, 62, 16, 5631. Preference is given to effecting the synthesis by reacting the corresponding secondary amines with hypochlorites, as described in JACS, 1973, 6400 or by Toshimasa et al. Bull. Chem. Soc. Jap., 1972, 45, 1802 and Deno et al. JACS 1971, 93, 2065.

A preferred embodiment of the invention relates to the calcium- or magnesium-complexed metal bisamides of the formula (I) and tautomers thereof, and to a process for preparation thereof, where AE is calcium or magnesium, M is a metal selected from Sc, Ti, Mn, Fe, Co, Ni, Cu, Zn and Al;

X is a halogen atom selected from chlorine and bromine;

$R^1$ and $R^2$ together form a —$(CH_2)_4$—, —$(CH_2)_5$— or —$(CH_2)_2O(CH_2)_2$— group in which each of these groups may optionally be substituted by 1, 2, 3 or 4 $R^4$ radicals; therein, $R^4$ is selected from methyl, ethyl, n-propyl and i-propyl.

A particularly preferred embodiment of the invention relates to the calcium- or magnesium-complexed metal bisamides of the formula (I) and tautomers thereof, and to a process for preparation thereof, where AE is calcium or magnesium, M is a metal selected from Ti, Mn, Fe, Zn and Al;

X is a halogen atom selected from chlorine and bromine, preferably chlorine;

$R^1$ and $R^2$ together form a —$(CH_2)_5$— group substituted by 4 methyl groups.

Very particular preference is given to using 1-chloro-2,2,6,6-tetramethylpiperidine as the chloroamine of the formula (II).

The process according to the invention is preferably executed within a temperature range from +20 to –20° C. The reaction is preferably effected at a temperature within the range from 10 to –10° C., more preferably from 5 to –5° C.

The reaction is preferably performed under protective gas atmosphere in an aprotic, anhydrous solvent preferably selected from the group consisting of ethers and aromatics, or else mixtures thereof. Particular preference is given to using coordinating solvents, for example THF, 2-methyltetrahydrofuran, tert-butyl methyl ether, 1,2-dimethoxyethane or diethyl ether, or else mixtures thereof with aromatics, for example benzene, toluene, ethylbenzene or xylene, and/or else with alkanes or cycloalkanes or alkyl-substituted cycloalkanes, for example n-hexane, n-heptane, cyclohexane, isooctane or methylcyclohexane. The dilution of the reaction mixture is preferably adjusted such that the resulting solution of the AE-complexed metal bisamide can be used in subsequent reactions without further concentration. In this case, preference is given to removing excess calcium or magnesium powder or calcium or magnesium halide and metal (M) or the metal halide ($M^{n+}X^-_n$) by filtration or decanting.

Based on the chloroamine of the formula (II), the metallic alkaline earth metal (AE) (i) and/or optionally the halide thereof ($AEX_2$) (ii) is used preferably in a (preferably slight) excess and the metal (M) (iv) and/or optionally the metal halide thereof ($M^{n+}X^-_n$) (iii) in deficiency.

According to the present invention, preference is given to using, for each equivalent (eq.) of the chloroamine of the formula (II), 0.2 to 5 equivalents, preferably 0.25 to 2 equivalents, more preferably 0.5 to 2 equivalents and especially preferably 0.5 to 1.5 equivalents of metallic magnesium and/or calcium (i) and/or the halides thereof (ii).

As an alternative to or in addition to the aforementioned equivalents of metallic magnesium and/or calcium and/or the halides thereof (ii), preference is given to using a substoichiometric amount of 0.5 to 0.9 equivalent, preferably 0.5 to 0.7 equivalent, more preferably 0.5 to 0.6 equivalent, of the metal halide ($M^{n+}X^-_n$) (iii).

As an alternative to or in addition to the aforementioned equivalents of metallic magnesium and/or calcium and/or the halides thereof (ii), preference is given to using a substoichiometric amount of 0.5 to 0.9 equivalent, preferably 0.5 to 0.7 equivalent, more preferably 0.5 to 0.6 equivalent, of the metal (M) (iv) in elemental form.

According to the present invention, in a preferred configuration, preference is given to using, for each equivalent of the chloroamine of the formula (II), 0.25 to 5 equivalents, preferably 0.4 to 2 equivalents, more preferably 0.5 to 1.5 equivalents, of metallic magnesium and/or calcium (i) and/or halides thereof (ii), and also, for each equivalent of the chloroamine of the formula (II), 0.4 to 6 equivalents, preferably 0.5 to 5 equivalents, more preferably 1 to 4 equivalents, of the metal (M) (iv) in elemental form.

According to the present invention, in a further preferred configuration, preference is given to using, for each equivalent of the chloroamine of the formula (II), 1 to 8 equivalents, preferably 2 to 6 equivalents, more preferably 3 to 5 equivalents, of the metal (M) (iv) in elemental form, and preference is given to using, for each equivalent of the chloroamine of the formula (II), 0.2 to 2 equivalents, preferably 0.25 to 1.5 equivalents, more preferably 0.3 to 0.9 equivalent and especially preferably 0.4 to 0.7 equivalent of metallic magnesium and/or calcium.

The alkaline earth metal can also be used in the form of mixtures of calcium and magnesium (i) or halides thereof (ii). The combined use of magnesium and calcium and/or halides thereof makes it possible to obtain mixtures of the compounds of the formula (I) which, owing to synergisms, may have advantages, for example elevated solubility.

Equally, it is also possible to use mixtures of metals (M) (iv) or halides thereof ($M^{n+}X^-_n$) (iii).

Metallic magnesium can be used in the reaction in the form of turnings, beads or powder. Owing to the high active surface area, magnesium powder is preferred.

Metallic calcium is typically used in the reaction in the form of calcium powder. In the context of the present invention, preference is given to using calcium fluoride, calcium chloride or calcium bromide, particular preference to using calcium chloride.

Magnesium halides are selected from magnesium fluoride, magnesium chloride, magnesium bromide and magnesium iodide. Preference is given to using magnesium chloride or magnesium bromide, particular preference to using magnesium chloride.

For further activation, it is optionally possible to add an activating reagent, alone or in combination, for example i-$Bu_2AlH$ (DIBAL-H), dibromoethane or iodine.

The metals (M) used in the context of the present invention are selected from metals of groups 3, 4, 7, 8, 9, 10, 11, 12, 13 of the Periodic Table of the Elements (IUPAC nomenclature) or the halides thereof, preferably chlorides, and the group of the lanthanoids or the halides thereof, preferably chlorides; the metals (M) are preferably selected from Sc, Ti, Mn, Fe, Co, Ni, Cu, Zn and Al or the halides thereof, preferably chlorides; the metals (M) are more preferably selected from Ti, Mn, Fe, Zn and Al or the halides thereof, preferably chlorides. In the context of the present invention, zinc and zinc chloride ($ZnCl_2$) are of outstanding significance. In addition, in the context of the present invention, manganese (Mn) and manganese halides, preferably $MnCl_2$, are of outstanding significance.

Preference is given to performing the process according to the invention by reaction of chloroamines of the formula (II) (as defined above) with
(i) metallic magnesium and/or calcium, and
(iv) an amount—preferably a substoichiometric amount based on the chloroamine of the formula (II)—of a metal (M) (i.e. in elemental form),
with optional additional use of
(ii) a magnesium and/or calcium halide
and/or
(iii) an preferably a substoichiometric amount based on the chloroamine of the formula (II)—of a metal halide ($M^{n+}X^-_n$),
where M and X are each as defined above, wherein preference is given to M and X as defined in a preferred embodiment mentioned above.

Due to their particularly beneficial and often superior properties, the present invention also relates to alkaline earth metal-complexed metal bisamides of the following formula (I-iii) and/or the tautomers, oligomers and/or polymers thereof

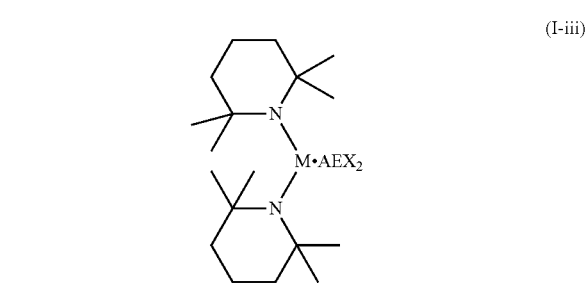

(I-iii)

wherein
AE is calcium or magnesium,
M is a metal selected from Sc, Ti, Mn, Fe, Co, Ni, Cu, Zn and Al;
X is a halogen atom selected from chlorine and bromine, more preferably chorine.

More particularly, the present invention also relates to the Mg-complexed zinc bisamide of the formula (I-iv) and the Ca-complexed zinc bisamide of the formula (I-v):

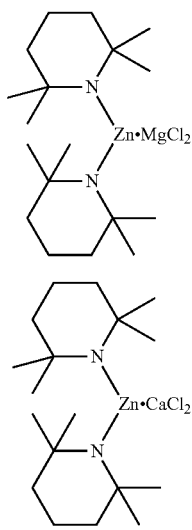

(I-iv)

(I-v)

The present invention further provides for the use of the inventive alkaline earth metal-complexed metal bisamides of the formula (I) as bases for metallation of aromatics and other organic compounds having activated C—H bonds. The basicity, selectivity or activity thereof can be enhanced or advantageously influenced by addition of lithium salts, for example lithium chloride, crown ethers or other coordinating reagents, during either the preparation or the use.

The present invention is to be illustrated in detail by the examples which follow.

EXAMPLES

Preparation of $(TMP)_2Zn.MgCl_2$ with 0.5 Eq. of Mg

In a dry, argon-filled Schlenk tube with a magnetic stirrer bar and septum, magnesium powder (325 mesh—243 mg, 10 mmol) and zinc powder (5231 mg, 80 mmol) were initially charged in anhydrous THF (15 ml) and activated by addition of DIBAL-H (0.1 ml, 1 M in THF). After stirring for 5 min, the mixture was cooled to 0° C. and the stirring was stopped. After the addition of iodine (65 mg, 0.25 mmol), the mixture was stirred again and 1-chloro-2,2,6,6-tetramethylpiperidine (TMPCl; 3.51 g, 20 mmol) in anhydrous THF (15 ml) was added dropwise at −5° C. with an infusion pump (rate: 15 ml/h). Thereafter, the reaction mixture was stirred at 25° C. for 30 min. Subsequently, the metal residues were decanted off and the yellow solution was titrated with benzoic acid and N-phenyl-4-(phenylazo)aniline as an indicator. The concentration was 0.48 M (yield=84% of theory).

Preparation of $(TMP)_2Zn.CaCl_2$ with 0.5 eq. of Ca

In a dry, argon-filled Schlenk tube with a magnetic stirrer bar and septum, calcium powder (16 mesh—401 mg, 10 mmol) and zinc powder (5231 mg, 80 mmol) were initially charged in anhydrous THF (15 ml) and activated by addition of DIBAL-H (0.1 ml, 1 M in THF). After stirring for 5 min, the mixture was cooled to 0° C. and the stirring was stopped. After the addition of iodine (65 mg, 0.25 mmol), the mixture was stirred again and 1-chloro-2,2,6,6-tetramethylpiperidine (TMPCl; 3.51 g, 20 mmol) in anhydrous THF (15 ml) was added dropwise at −5° C. with an infusion pump (rate: 15 ml/h). Thereafter, the reaction mixture was stirred at 25° C. for 30 min. Subsequently, the metal residues were decanted off and the yellow solution was titrated with benzoic acid and N-phenyl-4-(phenylazo)aniline as an indicator. The concentration was 0.50 M (yield=87% of theory).

Examples of the Zincation of Various Heteroaromatics

Preparation of 5-iodo-2,4,6-trichloropyrimidine

A dry, argon-filled Schlenk tube with a magnetic stirrer bar and septum is initially charged with 2,4,6-trichloropyrimidine (184 mg, 1 mmol) in anhydrous THF (1 ml). After adding $(TMP)_2Zn.MgCl_2$ (3.16 ml, 1.2 mmol) at 25° C., the mixture is stirred for 1 h. Then a solution of iodine (355 mg, 1.4 mmol), dissolved in anhydrous THF (2 ml), is added dropwise and the reaction mixture is stirred at 25° C. for 1 h. After dilution with aqueous sat. $NH_4Cl$ solution (30 ml) and extraction with ethyl acetate (3×30 ml), the combined organic phases are dried over $Na_2SO_4$, and distillative removal of the solvent and purification by column chromatography on silica gel (heptane:ethyl acetate) afforded the desired compound (240 mg, 78% of theory) as a colourless crystalline product.
$^{13}C$ NMR (100 MHz, $CDCl_3$): δ=167.6, 159.3, 96.5 ppm Preparation of 2-(3-fluorophenyl)-benzothiophene-3-carboxaldehyde A dry, argon-filled Schlenk tube with a magnetic stirrer bar and septum is initially charged with 1-benzothiophene-3-carbaldehyde (163 mg, 1 mmol) in anhydrous THF (1 ml). After adding $(TMP)_2Zn.MgCl_2$ (3.16 ml, 1.2 mmol) at 25° C., the mixture is stirred for 1 h, then a solution of 1-fluoro-3-iodobenzene (311 mg, 1.4 mmol), bis(dibenzylideneacetone) palladium(0) (17 mg, 3 mol %) and tri-2-furylphosphine (14 mg, 6 mol %) in anhydrous THF (2 ml) is added dropwise and the mixture is stirred at 25° C. overnight. For workup, the mixture is diluted with aqueous sat. $NH_4Cl$ solution (30 ml) and extracted with ethyl acetate (3×30 ml). After the combined organic phases have been dried over $Na_2SO_4$, the solvent has been distilled off and purification has been effected by column chromatography on silica gel (heptane:ethyl acetate), the desired compound (195 mg, 76% of theory) was obtained as a colourless crystalline product.
$^1H$ NMR (400 MHz, $CDCl_3$): δ in ppm=10.08 (s, 1H), 8.78 (d, 1H), 7.86 (d, 1H), 7.53 (m, 3H), 7.38 (m, 1H), 7.32 (m, 1H), 7.25 (m, 1H)

Preparation of 2-bromo-5-(4-chlorophenyl)-1,3-thiazole

A dry, argon-filled Schlenk tube with a magnetic stirrer bar and septum is initially charged with 1-benzothiophene-3-carbaldehyde (163 mg, 1 mmol) in anhydrous THF (2 ml). After adding $(TMP)_2Zn.MgCl_2$ (3.16 ml, 1.2 mmol) at 25° C., the mixture is stirred for 20 min, then a solution of 1-chloro-4-iodobenzene (358 mg, 1.5 mmol), bis(dibenzylideneacetone)palladium(0) (17 mg, 3 mol %) and tri-2-furylphosphine (14 mg, 6 mol %) in anhydrous THF (4 ml) is added dropwise and the mixture is stirred at 25° C. overnight. For workup, the mixture is diluted with aqueous sat. $NH_4Cl$ solution (30 ml) and extracted with ethyl acetate (3×30 ml). After the combined organic phases have been dried over $Na_2SO_4$, the solvent has been distilled off and purification has been effected by column chromatography on silica gel (heptane:ethyl acetate), the desired compound (195 mg, 71% of theory) was obtained as a colourless crystalline product.

$^1$H NMR (400 MHz, DMSO-$d_6$): δ in ppm=8.17 (s, 1H), 7.69 (d, 2H), 7.53 (d, 2H)

Preparation of 1,3-difluoro-2-iodo-4-nitrobenzene

A dry, argon-filled Schlenk tube with a magnetic stirrer bar and septum is initially charged with 2,4-difluoro-1-nitrobenzene (159 mg, 1 mmol) in anhydrous THF (2 ml). After adding (TMP)$_2$Zn.MgCl$_2$ (3.00 ml, 1.2 mmol) at 25° C., the mixture is stirred for 30 min, then a solution of iodine (381 mg, 1.5 mmol) in anhydrous THF (2 ml) is added dropwise and the mixture is stirred at 25° C. overnight. For workup, the mixture is diluted with aqueous sat. NH$_4$Cl solution (30 ml) and aqueous sat. Na$_2$S$_2$O$_3$ solution (30 ml) and extracted with ethyl acetate (3×30 ml). After the combined organic phases have been dried over Na$_2$SO$_4$, the solvent has been distilled off and purification has been effected by column chromatography on silica gel (heptane:ethyl acetate), the desired compound (210 mg, 74% of theory) was obtained as a colourless crystalline product.

$^1$H NMR (400 MHz, CDCl$_3$): δ in ppm=8.15 (m, 1H), 7.06 (m, 1H)

Preparation of tert-butyl 3-(3-fluorophenyl)prop-2-ynoate

A dry, argon-filled Schlenk tube with a magnetic stirrer bar and septum is initially charged with tert-butyl prop-2-ynoate (70 mg, 0.56 mmol) in anhydrous THF (2 ml). After adding (TMP)$_2$Zn.MgCl$_2$ (2.2 ml, 1.2 mmol) at 25° C., the mixture is stirred for 30 min, then a solution of 1-fluoro-3-iodobenzene (160 mg, 0.72 mmol), tetrakis(triphenylphosphine)palladium (0) (33 mg, 5 mol %) in anhydrous THF (2 ml) is added dropwise and the mixture is stirred at 25° C. overnight. For workup, the mixture is diluted with aqueous sat. NH$_4$Cl solution (30 ml) and extracted with ethyl acetate (3×30 ml). After the combined organic phases have been dried over Na$_2$SO$_4$, the solvent has been distilled off and purification has been effected by column chromatography on silica gel (heptane:ethyl acetate), the desired compound (91 mg, 75% of theory) was obtained as a colourless oil.

$^1$H NMR (400 MHz, CDCl$_3$): δ in ppm=7.34 (m, 2H), 7.26 (m, 1H), 7.13 (m, 1H), 1.53 (s, 9H)

Preparation of ethyl 4-(2-chloro-3-nitropyridin-4-yl)benzoate

A dry, argon-filled Schlenk tube with a magnetic stirrer bar and septum is initially charged with (TMP)$_2$Zn.MgCl$_2$ (3.16 ml, 1.2 mmol). After adding 2-chloro-3-nitropyridine (159 mg, 1 mmol) in anhydrous THF (2 ml) at 25° C., the mixture is stirred for 1 min, then a solution of ethyl 4-iodobenzoate (387 mg, 1.4 mmol), bis(dibenzylideneacetone)palladium(0) (17 mg, 3 mol %) and tri-2-furylphosphine (14 mg, 6 mol %) in anhydrous THF (2 ml) is added dropwise and the mixture is stirred at 25° C. for 1 h. For workup, the mixture is diluted with aqueous sat. NH$_4$Cl solution (30 ml) and extracted with ethyl acetate (3×30 ml). After the combined organic phases have been dried over Na$_2$SO$_4$, the solvent has been distilled off and purification has been effected by column chromatography on silica gel (heptane:ethyl acetate), the desired compound (177 mg, 58% of theory) was obtained as a yellowish oil.

$^1$H NMR (400 MHz, CDCl$_3$): δ in ppm=7.80 (d, 1H), 7.79 (d, 1H), 7.76 (d, 1H), 7.74 (d, 1H), 4.37 (q, 2H), 1.39 (t, 3H).

The invention claimed is:

1. Process for preparing an alkaline earth metal-complexed metal bisamide of formula (I) and/or a tautomer thereof

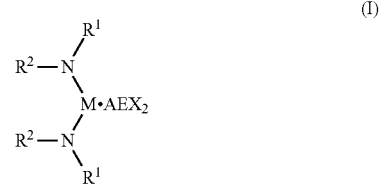

where
AE is an alkaline earth metal selected from calcium and magnesium;
M is a metal selected from metals from groups 3, 4, 7, 8, 9, 10, 11, 12, 13 of the Periodic Table of the Elements and the group of the lanthanoids;
X is a halogen atom selected from the group consisting of fluorine, chlorine, bromine and iodine;
$R^1$ and $R^2$ are each independently selected from the group consisting of ($C_1$-$C_8$)alkyl optionally substituted by 1-2 $R^3$ radicals;
$R^3$ is independently selected from halogen, ($C_1$-$C_3$)alkoxy, ($C_1$-$C_3$)haloalkoxy and ($C_2$-$C_4$)dialkylamino;
or
$R^1$ and $R^2$ together form a —(CH$_2$)$_4$—, —(CH$_2$)$_5$— or —(CH$_2$)$_2$O(CH$_2$)$_2$— group, where each of these groups may optionally be substituted by 1-4 $R^4$ radicals;
$R^4$ is selected from halogen, ($C_1$-$C_3$)alkyl, ($C_1$-$C_3$)alkoxy, ($C_1$-$C_3$)haloalkoxy and ($C_2$-$C_4$)dialkylamino or ($C_2$-$C_4$) alkoxycarbonyl,
by reacting a chloroamine of formula (II)

in which the $R^1$ and $R^2$ radicals are each as defined above with
(i) metallic magnesium and/or calcium and/or
(ii) a magnesium and/or calcium halide and
(iii) an amount of a metal halide ($M^{n+}X^-_n$) and/or
(iv) an amount of a metal (M),
where M and X are each as defined above.

2. Process according to claim 1, where
AE is an alkaline earth metal selected from calcium and magnesium;
M is a metal selected from Sc, Ti, Mn, Fe, Co, Ni, Cu, Zn and Al;
X is a halogen atom selected from chlorine and bromine;
$R^1$ and $R^2$ together form a —(CH$_2$)$_4$—, —(CH$_2$)$_5$— or —(CH$_2$)$_2$O(CH$_2$)$_2$— group, where each of these groups may optionally be substituted by 1-4 $R^4$ radicals;
$R^4$ is selected from methyl, ethyl, n-propyl and i-propyl.

3. Process according to claim 1, where
AE is an alkaline earth metal selected from calcium and magnesium;
M is a metal selected from Ti, Mn, Fe, Zn and Al;
X is chlorine;

R[1] and R[2] together form a —(CH$_2$)$_5$— group substituted by 4 methyl groups.

4. Process according to claim 1, where

AE is calcium or magnesium,

M is zinc or manganese;

X is chlorine; and

R[1] and R[2] together form a —C(CH$_3$)$_2$(CH$_2$)$_3$—C(CH$_3$)$_2$— group.

5. Process according to claim 1, where

AE is calcium or magnesium;

M is zinc;

X is chlorine; and

R[1] and R[2] together form a —C(CH$_3$)$_2$(CH$_2$)$_3$—C(CH$_3$)$_2$— group.

6. Process according to claim 1, wherein said process is executed within a temperature range from +20 to −20° C.

7. Process according to claim 1, wherein the reaction is performed in a coordinating solvent selected from THF, 2-methyltetrahydrofuran, t-butyl methyl ether, 1,2-dimethoxyethane, diethyl ether, di-n-butyl ether and methyl cyclopentyl ether, or mixtures thereof.

8. Process according to claim 1, wherein the reaction is performed in a mixture of a coordinating solvent selected from THF, 2-methyltetrahydrofuran, t-butyl methyl ether, 1,2-dimethoxyethane, di-n-butyl ether, methyl cyclopentyl ether and/or diethyl ether, and one or more noncoordinating solvents selected from aromatics and alkyl-substituted aromatics, preferably benzene, toluene, xylene and/or ethylbenzene, and alkanes, cycloalkanes and/or alkyl-substituted cycloalkanes, optionally cyclohexane, n-heptane, isooctane and/or methylcyclohexane.

9. Process according to claim 1 for preparation of an AE-complexed metal amide of the formula (I), wherein the process is performed in the presence of one or more lithium salts.

10. Alkaline earth metal-complexed metal bisamide of formula (I) and/or a tautomer, oligomer and/or polymer thereof

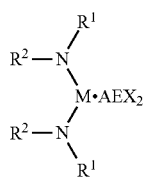

(I)

where

AE is an alkaline earth metal selected from calcium and magnesium;

M is a metal selected from metals from groups 3, 4, 7, 8, 9, 10, 11, 12, 13 of the Periodic Table of the Elements and the group of the lanthanoids;

X is a halogen atom selected from the group consisting of fluorine, chlorine, bromine and iodine;

R[1] and R[2] are each independently selected from the group consisting of (C$_1$-C$_8$)alkyl optionally substituted by 1-2 R[3] radicals;

R[3] is independently selected from halogen, (C$_1$-C$_3$)alkoxy, (C$_1$-C$_3$)haloalkoxy and (C$_2$-C$_4$)dialkylamino;

or

R[1] and R[2] together form a —(CH$_2$)$_4$—, —(CH$_2$)$_5$— or —(CH$_2$)$_2$O(CH$_2$)$_2$— group, where each of these groups may optionally be substituted by 1-4 R[4] radicals;

R[4] is selected from halogen, (C$_1$-C$_3$)alkyl, (C$_1$-C$_3$)alkoxy, (C$_1$-C$_3$)haloalkoxy and (C$_2$-C$_4$)dialkylamino or (C$_2$-C$_4$) alkoxycarbonyl.

11. Alkaline earth metal-complexed metal bisamide of formula (I-iii) and/or a tautomer, oligomer and/or polymer thereof

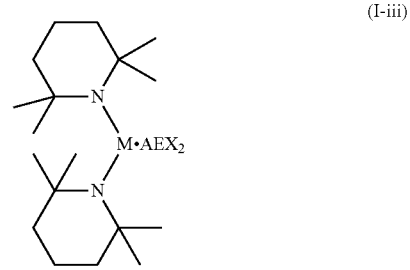

(I-iii)

where

AE is calcium or magnesium,

M is a metal selected from Sc, Ti, Mn, Fe, Co, Ni, Cu, Zn and Al;

X is a halogen atom selected from chlorine and bromine.

12. Mg-complexed zinc bisamide of the formula (I-iv)

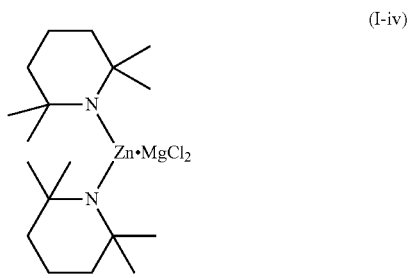

(I-iv)

13. Ca-complexed zinc bisamide of the formula (I-v)

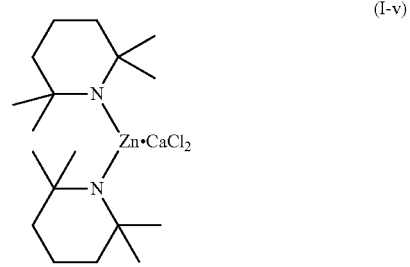

(I-v)

14. An alkaline earth metal-complexed metal bisamide of the formula (I), according to claim 10 capable of being used as a base for metallation of one or more aromatics, heteroaromatics, alkenes, alkynes and/or other organic compounds having activated C—H bonds.

* * * * *